(12) United States Patent
Hölzer et al.

(10) Patent No.: US 7,396,952 B2
(45) Date of Patent: Jul. 8, 2008

(54) PROCESS FOR PREPARING CARBAMIC ESTER DERIVATIVES

(75) Inventors: Bettina Hölzer, Leverkusen (DE); Herbert Diehl, Leverkusen (DE)

(73) Assignee: LANXESS Deutschland GmbH, Leverkusen (DE)

( * ) Notice: Subject to any disclaimer, the term of this patent is extended or adjusted under 35 U.S.C. 154(b) by 338 days.

(21) Appl. No.: 11/295,394

(22) Filed: Dec. 6, 2005

(65) Prior Publication Data

US 2007/0232825 A1  Oct. 4, 2007

(30) Foreign Application Priority Data

Dec. 10, 2004 (DE) ................. 10 2004 059 470

(51) Int. Cl.
  *C07C 261/00* (2006.01)
(52) U.S. Cl. ........................................ 560/24
(58) Field of Classification Search ............. None
See application file for complete search history.

(56) References Cited

U.S. PATENT DOCUMENTS

2003/0013707 A1   1/2003  Hodson et al. .......... 514/230.5

FOREIGN PATENT DOCUMENTS

| EP | 034 292 | 8/1981 |
| WO | 97/28118 | 8/1997 |

OTHER PUBLICATIONS

Yadav et al., New Journal of Chemistry (2000), 24(8), 571-573.*
J. Org. Chem. 1952, 17, 141 B. R. Baker et al.; "An Antimalarial Alkaloid From Hydrangea, XIV, Synthesis of 5- ,6-,7-, and 8-Monosubstituted Derivatives".
J. Org. Chem. 1978, vol. 43, No. 2, 220 T.H. Fisher et al.; "Kinetic Study of the N-Bromosuccin-imide Bromination of Some 4-Substituted 3-Cyanotoluenes".
Chem. Ber. 1909, 42, 430.
J. Chem. Soc. Perkin I, 1973, 2940; Peter H. Gore et al. Friedel-Crafts Reactions, Part XXV.[1] Acetylation and Benzoylation of Iodobenzene and of o-, m-, and p- Iodotoluenes.
Monatsch. Chem. 1920, 41, 155.
J. Org. Chem. 1981, 46, 4614-4617 Donald Valentine, Jr. et al; "Practical, Catalytic Synthesis of Anthranilic Acids".
Thomas G. Back et al.: "Conjugate Additions of o-Iodoanilines and Methyl Anthranilates to Acetylenic Sulfones. A New Route to Quinolones Including First Syntheses of Two Alkaloids from the Medical Herb Ruta chalepensis" Journal of Organic Chemistry., Bd. 68, 2003, Seiten 2223-2233, XP002371555 US American Chemical Society, Easton. Seite 2227, Spalte 1, Reaktionsschema 4 und Spalte 2, Zeile 8-Zeile 9; Seite 2231, Spalte 2, Zeile 43-Zeile 54.

* cited by examiner

*Primary Examiner*—Karl Puttlitz
(74) *Attorney, Agent, or Firm*—Michael A. Miller

(57) ABSTRACT

An improved process for preparing carbamic ester derivatives of the general formula (1)

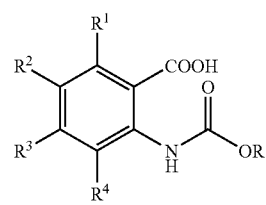

(1)

by reaction with carbon monoxide and water in the presence of a palladium catalyst is provided.

1 Claim, No Drawings

PROCESS FOR PREPARING CARBAMIC ESTER DERIVATIVES

FIELD OF THE INVENTION

The present invention relates to a novel process for preparing carbamic ester derivatives of the general formula (1)

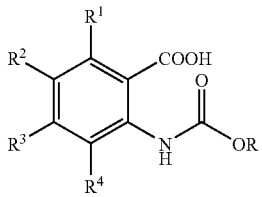

(1)

and to the novel compound hexadecyl (2-bromo-4-methylphenyl)carbamate (2″)

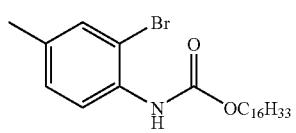

(2″)

BACKGROUND OF THE INVENTION

Carbamic ester derivatives of the general formula (1) and especially (2-carboxy-4-methylphenyl)carbamic esters of the general formula (1')

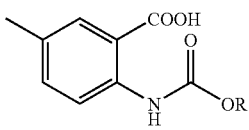

(1')

are suitable intermediates for active pharmaceutical ingredients.

Thus, for example, hexadecyl (2-carboxy-4-methylphenyl)carbamate as compound of the formula (1') with $R=C_{16}H_{33}$ is disclosed as an intermediate in the preparation of 2-hexadecyloxy-6-methyl-4H-3,1-benzoxazin-4-one of the formula (3)

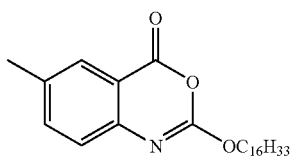

(3)

from the originally published version of WO-A 00/40569. 2-Hexadecyloxy-6-methyl-4H-3,1-benzoxazin-4-one of the formula (3) is described therein as potential active ingredient for the treatment of obesity and type II diabetes. In this originally published version of WO-A 00/40569, two synthetic routes 1 and 2 are described for preparing 2-hexadecyloxy-6-methyl-4H-3,1-benzoxazin-4-one (3), each of which starts from the 5-methyl-substituted anthranilic acid (4).

In the two-stage synthetic route 1, the 5-methyl-substituted anthranilic acid (4) is reacted with hexadecyl chloroformate (5) and subsequently with methyl chloroformate to give 2-hexadecyloxy-6-methyl-4H-3,1-benzoxazin-4-one (3), although the overall yield obtained is only 31%.

The one-stage synthetic route 2 with an excess of pyridine affords 2-hexadecyl-oxy-6-methyl-4H-3,1-benzoxazin-4-one (3) in an even lower yield of 15%.

Synthetic route 1:

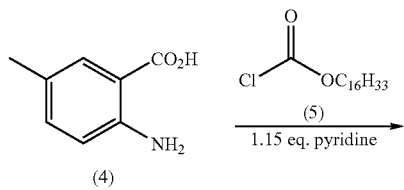

(4)

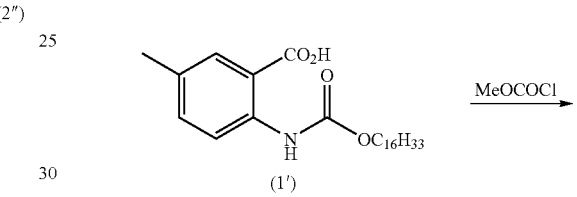

(1')

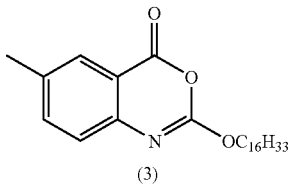

(3)

Synthetic route 2:

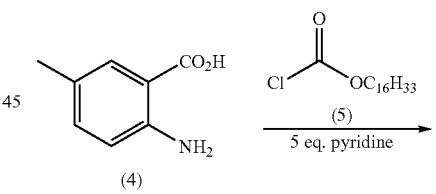

(4)

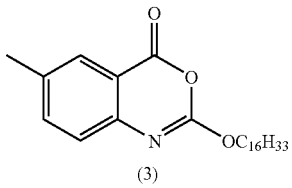

(3)

The starting compound which is required for both the synthetic routes 1 and 2, the 5-methyl-substituted anthranilic acid (4), is not easily obtainable, however.

It is prepared by the method described in J. Org. Chem. 1952, 17, 141. This starts from p-toluidine, which is reacted with chloral hydrate and hydroxylamine hydrochloride. The resulting oxime is cyclized with acid catalysis, and subsequently the ring is cleaved again by oxidation under basic conditions.

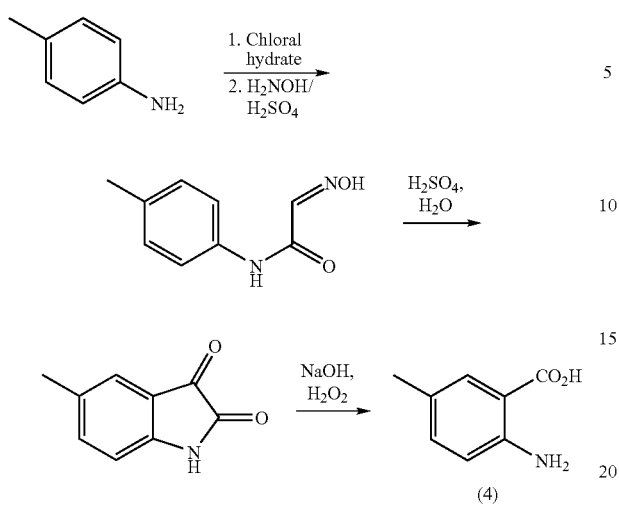

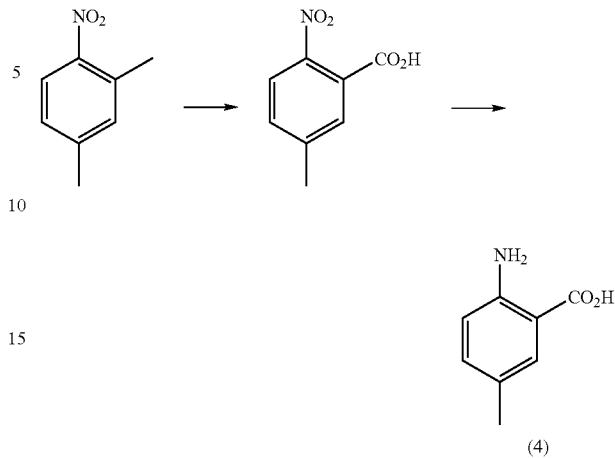

The disadvantages of this synthesis are the low yields and the fact that only very low concentrations can be used. For this reason, this synthetic route is unattractive for an industrial reaction.

Further alternative routes known in principle for obtaining anthranilic acids are as follows:

J. Org. Chem. 1978, 43, 220 and Chem. Ber. 1909, 42, 430 disclose initial nitration of 3-cyanotoluene, then reduction of the nitro group and subsequent hydrolysis of the nitrile to the carboxylic acid.

A disadvantage of this synthesis is that the nitration of 3-cyanotoluene does not proceed selectively and therefore a further purification step is necessary. This requires additional effort and reduces the yield.

The synthesis which is described in J. Chem. Soc. Perkin I, 1973, 2940 and which starts from 3-toluic acid with subsequent nitration and reduction of the nitro group also has the same disadvantage.

The synthesis which is disclosed in Monatsh. Chem. 1920, 41, 155 and starts from 2,4-dimethyl-1-nitrobenzene is likewise unsuitable because oxidation of the methyl group next to the nitro group does not proceed selectively and therefore an elaborate separation of isomers is necessary.

EP-A 0 034 292 discloses a process for preparing optionally substituted anthranilic acids which includes a transition metal-catalysed carbonylation reaction with carbon monoxide to give an anthranilic acid derivative. This carbonylation reaction takes place in an aqueous reaction medium containing a trialkylamine and a catalyst formed from palladium and a tertiary phosphine. The anthranilic acid derivatives can be obtained by eliminating the protective group. The precursors employed for the carbonylation are obtained starting from optionally substituted anilines as shown in principle in the reaction scheme below:

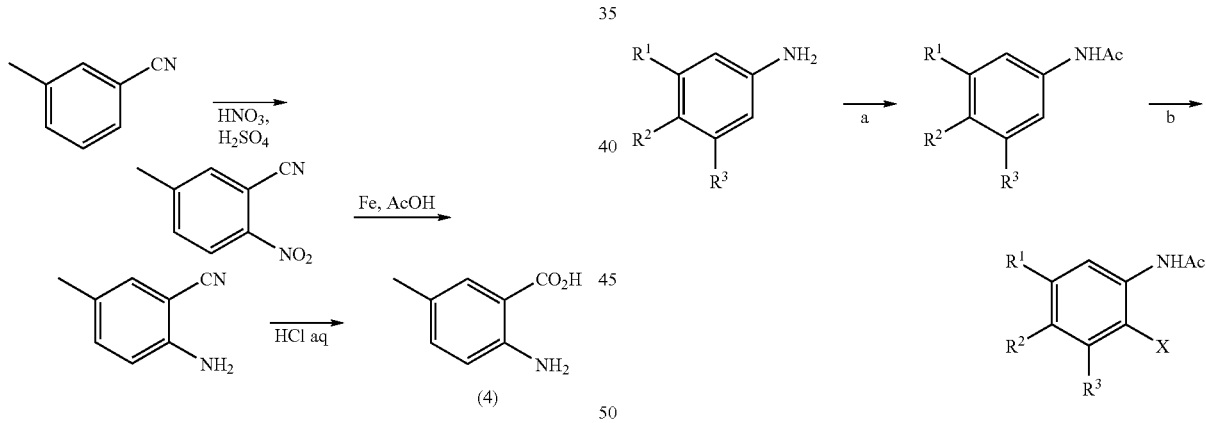

$R^1, R^2, R^3$ = H, alkyl, alkoxy, carboxyl, chlorine, fluorine, substituted phenyl;
X = halogen EP-A 0 034 292 describes this reaction sequence of acetylation (a), halogenation (b), carbonylation (c) and subsequent elimination of the acetyl group (d) as affording the optionally substituted anthranilic acids in good yields (>80%). However, the introduction of the acetyl group is a disadvantage. This is necessary because the free anilines give only poor yields in transition metal-catalysed carbonylation reactions because of pronounced complexation [J. Org. Chem. 1981, 46, 4614-4617].

WO-A 97/28118 discloses a comparable process.

Because of the diverse difficulties, described above, associated with the known processes for preparing optionally substituted anthranilic acids and the yields, which are only unsatisfactory and thus limiting for the overall process, of the subsequent synthetic routes 1 and 2, the object of the present invention was to provide an improved process for preparing carbamic ester derivatives of the general formula (1).

SUMMARY OF THE INVENTION

The present invention relates to a process for preparing carbamic ester derivatives of the general formula (1)

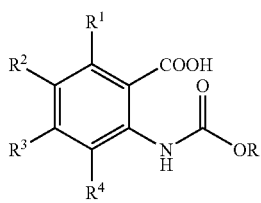

in which
$R^1$, $R^2$, $R^3$, $R^4$ are identical or different and are hydrogen, an alkyl, alkoxy, carboxyl, chlorine, fluorine radical or a phenyl radical which is optionally substituted by alkyl or alkoxy radicals, and
R is an alkyl, aryl or heteroaryl radical
by reacting compounds of the general formula (2)

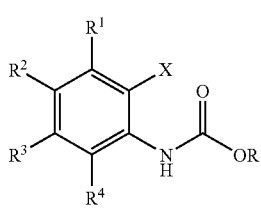

where
X is bromine or iodine, and
$R^1$, $R^2$, $R^3$, $R^4$ and R have the meanings stated for the general formula (1), with carbon monoxide and water in the presence of a palladium catalyst.

DETAILED DESCRIPTION OF THE INVENTION

The fact that the preparation of the carbamic ester derivatives of the general formula (I) is possible by the carbonylation according to the invention was surprising and not predictable on the basis of the prior art.

Carbonylation of an aromatic halogen compound with a carbamate side chain, in particular in the ortho position to the halogen radical and with a free NH group is not disclosed in the literature, and it is surprising that this carbonylation is possible with excellent results because the difficulties associated with palladium-catalysed carbonylation reactions of 2-haloanilines are well known, and a carbamate group as present in compound (2) has a stronger complexing effect than an acetyl group.

The substituents mentioned for the compounds of the general formula (2) employed in the process of the invention, and for the corresponding resulting compounds of the general formula (1), have the following meanings:

Alkyl for the purposes of this invention is a straight-chain or branched alkyl radical having 1 to 22 carbon atoms such as methyl, ethyl, and the straight-chain or all the branched radicals of propyl, butyl, pentyl, hexyl, heptyl, octyl, nonyl, decyl, undeceyl, dodecyl, tridecyl, tetradecyl, pentadecyl, hexadecyl, heptadecyl, octadecyl, nonadecyl, eicosyl or docosyl radicals.

For the radicals $R^1$, $R^2$, $R^3$ and $R^4$, alkyl is preferably a straight-chain or branched alkyl radical having 1 to 7 carbon atoms, particularly preferably methyl, ethyl, n-propyl, isopropyl, n-butyl, isobutyl or tert-butyl.

Alkyl for the radical R is preferably a straight-chain or branched alkyl radical having 16-22 carbon atoms.

Alkoxy for the purposes of this invention is preferably a straight-chain or branched alkoxy radical having 1 to 7 carbon atoms. Preference is given to a straight-chain or branched alkoxy radical having 1 to 4, particularly preferably having 1 to 3 carbon atoms. Preferred examples which may be mentioned are: methoxy, ethoxy, n-propoxy, isopropoxy, n-butoxy, isobutoxy, tert-butoxy, n-pentoxy, n-hexoxy and n-heptoxy.

Heteroaryl for the purposes of this invention is preferably an aromatic, mono- or bicyclic radical having 5 to 10 ring atoms and up to 5 heteroatoms from the series S, O and/or N. 5- to 6-membered heteroaryls having up to 4 heteroatoms are preferred. The heteroaryl radical may be bonded via a carbon atom or heteroatom. Preferred examples which may be mentioned are: thienyl, furyl, pyrrolyl, thiazolyl, oxazolyl, imidazolyl, pyridyl, pyrimidyl, pyridazinyl, indolyl, indazolyl, benzofuranyl, benzothiophenyl, quinolinyl and isoquinolinyl.

In a particularly preferred variant of the process of the invention, a compound of the general formula (2')

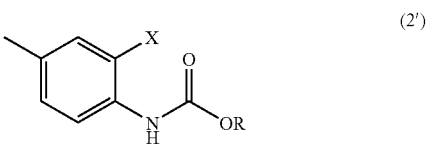

in which
X is chlorine or bromine, in particular bromine and
R is a straight-chain or branched alkyl radical having 16-22 carbon atoms, preferably a straight-chain alkyl radical having 16 carbon atoms, is reacted with carbon monoxide and water in the presence of a palladium catalyst to give a carbamic ester derivative of the general formula (1')

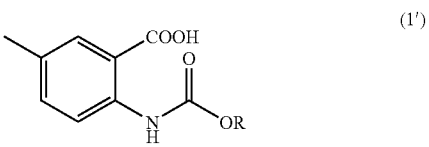

where

R has the meaning stated for the general formula (2').

Palladium catalysts which can be employed in the process of the invention for preparing the carbamic ester derivatives of the general formula (1) are for example those of the type $X_2Pd(PPh_3)_2$, where Ph is an optionally substituted phenyl radical, and X is halogen, preferably chlorine or bromine. These palladium catalysts can either be added as such to the reaction mixture or else favourably also be prepared in situ from $PdX_2$ and $PPh_3$. The $PPh_3$ component can in this case also be employed in excess. Based on the compound of the general formula (2), for example 0.1 to 1 mol %, preferably 0.1 to 0.5 mol %, of palladium catalyst is employed.

The process of the invention is normally carried out in the presence of a base. It is possible to employ as base for example primary, secondary and tertiary amines, acetates, carbonates and bicarbonates. Carbonates and bicarbonates are preferred. Based on 1 mole of the compound of the general formula (2) it is possible to employ for example 0.9 to 5 mol, preferably 1.0 to 2.0 mol of base.

The reaction temperature is not critical. The process of the invention is normally carried out at a reaction temperature in the range from 60 to 120° C., preferably in the range from 80 to 115° C. The reaction pressure is normally from 2 to 30 bar, preferably 2-15 bar.

The process of the invention is normally carried out in such a way that the compound of the general formula (2) is introduced together with the palladium catalyst as such or its precursors $PdX_2$ and $PPh_3$ into a pressure vessel, then water is added and, where appropriate, the base. The mixture is then heated to 60 to 120° C., and 2 to 30 bar of carbon monoxide are metered in, and this pressure is maintained until no further carbon monoxide is absorbed.

It is possible where appropriate to improve the solubility by using a mixture of one or more solvents with water. Preferred additional solvents are nitriles such as acetonitrile, amides such as dimethylformamide, ethers such as dioxane and tetrahydrofuran and branched, higher alcohols which do not compete with the water as nucleophile.

Preparation of the compounds of the general formula (2)

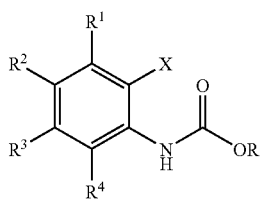

(2)

is possible by two different synthetic routes, both of which start from an optionally substituted aniline.

In synthetic route A, the compounds of the general formula (2) are prepared by an optionally substituted aniline of the general formula (6)

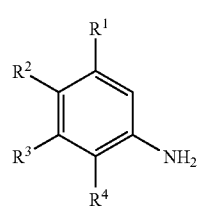

(6)

either

Ia) being reacted with phosgene or a substance which generates phosgene in situ or comprises phosgene, and Ib) the compound of the general formula (7) obtained in this way

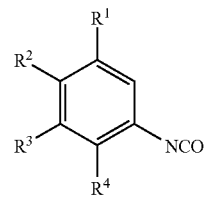

(7)

being reacted with an alcohol of the formula ROH or

II) being reacted with a compound of the formula Cl—C(=O)OR and the compound of the general formula (8) obtained both by step (Ia) and (Ib), and the alternative step (II),

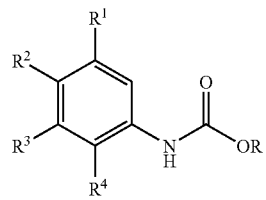

(8)

being subjected to a halogenation to form a compound of the general formula (2), where the radicals $R^1$, $R^2$, $R^3$, $R^4$ and R in all the abovementioned formulae have the meanings stated for the general formula (1).

Synthetic route A can also be depicted diagrammatically as follows:

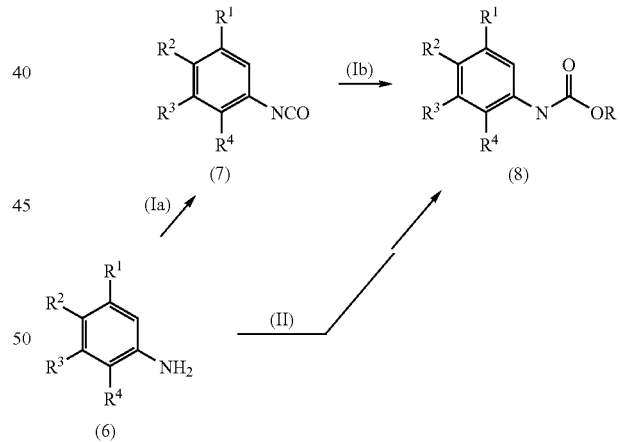

Steps (Ia) and (Ib) are carried out by analogous application of the disclosure present in Chem. Ber. 1888, 21, 411 and Bull. Soc. Chim. Fr. 1904, 31, 50.

An example of a substance which can be employed for generation of phosgene in situ is trichloromethyl chloroformate (diphosgene). An example of a phosgene-containing substance which can be employed is oxalyl chloride, which in technical quality frequently contains minor amounts of phosgene.

Step (II) is carried out with analogous application of the disclosure made in Chem. Ber. 1870, 3, 655.

The subsequent halogenation is carried out by methods known to the skilled person. The preferred bromination of the compounds of the general formula (9) can be carried out with use of Br$_2$/HOAc or Br$_2$H$_2$O$_2$/HOAc likewise by methods known to the skilled person.

In synthetic route B, the compounds of the general formula (2) are prepared by an optionally substituted aniline of the general formula (6)

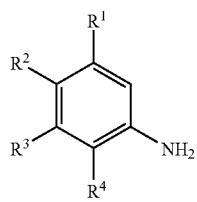

(6)

1) being subjected to a halogenation and
2) the compound of the general formula (9) obtained in this way

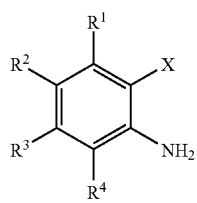

(9)

either

IIIa) being reacted with phosgene or with a substance which generates phosgene in situ or comprises phosgene, and IIIb) the compound of the formula (10) obtained in this way

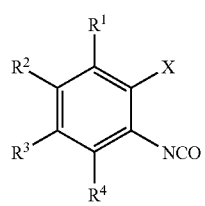

(10)

being reacted with an alcohol of the formula ROH or

IV) being reacted in a single step with Cl—C(=O)OR, where the radicals R$^1$, R$^2$, R$^3$, R$^4$ and R in all the abovementioned formulae have the meanings stated for the general formula (1).

The halogenation in step 1 of synthetic route B is carried out in analogy to Organic Syntheses, Coll. Vol. 1, p. 111.

The reaction in synthetic route B, step IIIa is carried out in analogy to Bioorg. Med. Chem. 1999, 7, 1597. An example of a substance which can be employed for generation of phosgene in situ is trichloromethyl chloroformate (diphosgene). An example of a phosgene-containing substance which can be employed is oxalyl chloride, which in technical quality frequently contains minor amounts of phosgene.

The reaction in synthetic route B, step IIIb is carried out in analogy to the disclosure present in Bull. Soc. Chim. Fr. 1904, 31, 50.

The reaction in synthetic route B, step IV, is carried out in analogy to the disclosure present in Chem. Ber. 1870, 3, 655.

The present invention relates further to the compound of the formula (2″)

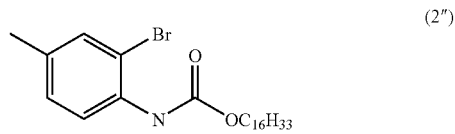

(2″)

This compound is important because the specific approach to 2-hexadecyloxy-6-methyl-4H-3,1-benzoxazin-4-one of the formula (3) is possible therewith by the described synthetic routes in a distinctly simpler form than by previous routes passing through the intermediate hexadecyl (2-carboxy-4-methylphenyl)carbamate. These routes proceed without formation of incorrect isomers, i.e. no elaborate purification or crystallization steps are therefore necessary.

The present invention further makes it possible to prepare 2-alkyloxy-6-methyl-4H-3,1-benzoxazin-4-ones of the general formula (11)

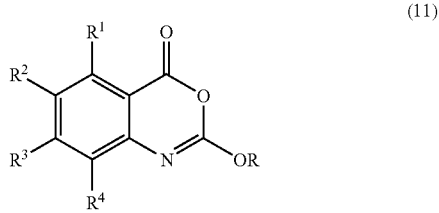

(11)

by reacting compounds of the general formula (2)

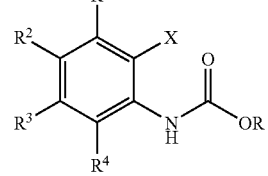

(2)

with carbon monoxide and water in the presence of a palladium catalyst to form carbamic ester derivatives of the general formula (1)

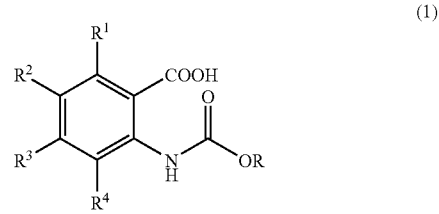

(1)

and reaction thereof with methyl or ethyl chloroformate, where R$^1$, R$^2$, R$^3$, R$^4$ and R in all the abovementioned formulae always have the meanings stated for the general formula (1).

The abovementioned reaction with methyl or ethyl chloroformate takes place by methods familiar to the skilled person.

The advantage of this overall process is that the additional introduction and elimination of the acetyl group as protective group for the carbonylation can be avoided. Instead, the 2-halo compound of the general formula (2) is employed directly in the carbonylation reaction. The omission of the elimination of the acetyl group makes a shorter and thus more economically attractive synthesis possible.

A further advantage of this synthetic route, especially in the preparation of hexadecyl (2-bromo-4-methylphenyl)carbamate (2″), is that, taking account of the preceding synthetic routes as described above starting from p-toluidine which is commercially available as pure isomer, no isomer problem exists as in the case of a route starting from 3-cyanotoluene or 3-toluic acid.

EXAMPLES

Example 1

Synthesis of hexadecyl 4-methylphenylcarbamate

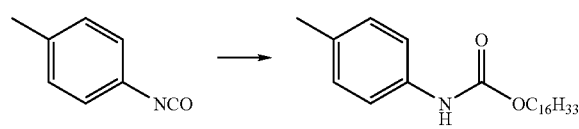

91 g (375 mmol) of 1-hexadecanol were added to a solution of 50 g (375 mmol) of p-tolyl isocyanate in 50 ml of toluene, and the resulting solution was heated under reflux for 8 h. After cooling to room temperature and stirring at this temperature for 12 h, the precipitated solid was filtered off. The colourless solid was washed twice with 10 ml of toluene each time and then dried in vacuo. 80 g (213 mmol, 57%) of the desired carbamate were obtained in the form of a colourless solid with a melting point of 75° C. The melting point agreed with literature data (75-76° C., Microchem J. 1962, 6, 179).

$^1$H-NMR (CDCl$_3$, 400 MHz): δ=0.88 ppm (t, J=7.3 Hz, 3H), 1.25-1.40 (m, 26 H), 1.66 (sext, J=6.9 Hz, 2H), 2.30 (s, 3H), 4.14 (t, J=6.9 Hz, 2H), 6.53 (br, 1 H), 7.10 (d, J=7.8 Hz, 2H), 7.25 (d, J=8.3 Hz, 2H). Elemental Analysis Showed: Calculated: C 76.8%, H 11.0%, N 3.7% Found: C 76.9%, H 11.2%, N 3.7%.

Example 2

Synthesis of hexadecyl (2-bromo-4-methylphenyl)carbamate

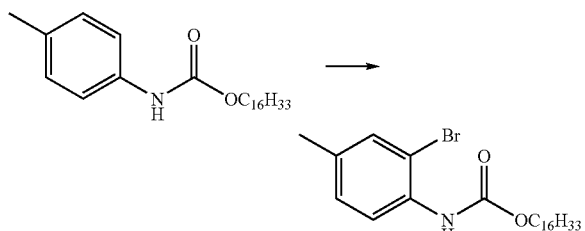

19 g (119 mmol) of bromine were added dropwise to a solution of 45 g (119 mmol) of the carbamate in 225 ml (235 g) of glacial acetic acid at room temperature over the course of 1 h, and then the resulting solution was stirred at room temperature for 1 h. After addition of a further 25 ml (26 g, 437 mmol) of glacial acetic acid, the reaction mixture was stirred at 40° C. for 5 h and then cooled to room temperature. The precipitated solid was filtered off and washed with 20 ml of glacial acetic acid. Drying in vacuo resulted in 40 g (88 mmol, 74%) of the desired bromo compound in the form of a colourless solid with a melting point of 57° C.

$^1$H-NMR (CDCl$_3$, 400 MHz): δ=0.93 ppm (t, J=6.6 Hz, 3H), 1.25-1.43 (m, 26 H), 1.73 (sext, J=6.8 Hz, 2H), 2.33 (s, 3H), 4.21 (t, J=6.7 Hz, 2H), 7.04 (br, 1H), 7.14 (d, J=8.4 Hz, 1H), 7.37 (s, 1H), 8.02 (d, J=8.3 Hz, 1H). $^{13}$C-NMR (CDCl$_3$, 100 MHz): δ=14.2 ppm, 20.4, 22.7. 25.9, 29.0, 29.3, 29.4, 29.6 (2C), 29.7 (2C), 29.8 (4C), 32.0, 65.7, 112.5, 120.3, 129.0, 132.5, 133.5, 134.1, 153.5. Elemental Analysis Showed: Calculated: C 63.4%, H 8.9%, N 3.1% Found: C 63.6%, H 8.9%, N 3.1%.

Example 3

Synthesis of 2-hexadecyloxycarbonylamino-5-methylbenzoic acid

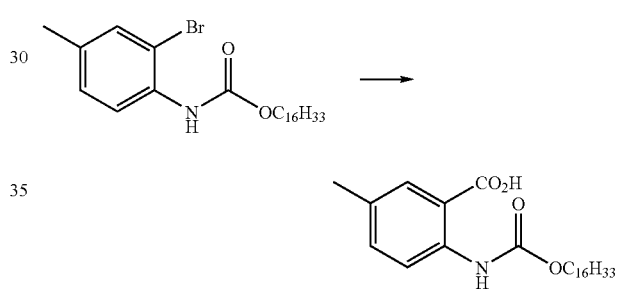

217.5 g (478.5 mmol) of hexadecyl (2-bromo-4-methylphenyl)carbamate, 0.5 g (0.7 mmol) of bis(triphenylphosphine)palladium dichloride and 2.5 g (9.3 mmol) of triphenylphosphine were introduced into an autoclave. The autoclave was closed, flushed with nitrogen and an oxygen-free solution of 78.1 g (565.3 mmol) of potassium carbonate in 400 ml of water is added. The autoclave is evacuated and then 2 bar of carbon monoxide are injected and heated to 115° C. The pressure is subsequently adjusted to 8 bar. After CO uptake ceases, the mixture is cooled to RT and 200 ml of toluene are added. The pH is adjusted to 2 with 2M aqueous HCl solution, and the organic phase is separated off. The aqueous phase is extracted anew with 100 ml of toluene, the organic phase is separated off, and the two toluene extracts are combined. Removal of the solvent in vacuo results in 154.9 g (369.2 mmol, 77%) of 2-hexadecyloxycarbonylamino-5-methylbenzoic acid in the form of a pale yellow-coloured solid.

$^1$H-NMR (CDCl$_3$, 400 MHz): δ=0.88 ppm (t, J=6.7 Hz, 3H), 1.24-1.40 (m, 26 H), 1.70 (sext, J=6.8 Hz, 2H), 2.33 (s, 3H), 4.17 (t, J=6.8 Hz, 2H), 7.38 (d, J=8.7 Hz, 1H), 7.90 (s, 1H), 8.35 (d, J=8.6 Hz, 1H). Signal of the NH proton not identifiable. $^{13}$C-NMR (CDCl$_3$, 100 MHz): δ=14.1 ppm, 20.5, 22.7. 25.9, 29.0, 29.3, 29.4, 29.6 (2 C), 29.7 (6 C), 32.0, 65.5, 113.6, 119.0, 131.1, 131.8, 136.3, 140.1, 153.9, 172.5.

Example 4

Synthesis of 2-hexadecyloxy-6-methyl-4H-3,1-benzoxazin-4-one

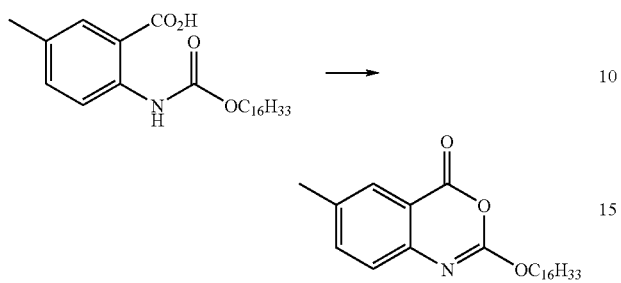

4.0 g (10.0 mmol) of 2-hexadecyloxycarbonylamino-5-methylbenzoic acid are introduced into 20 ml of pyridine at 0° C. under a nitrogen atmosphere, and 4.93 g (45.4 mmol) of ethyl chloroformate are added dropwise to the resulting solution at 0° C. over the course of 20 min. After the reaction mixture has been stirred at 0° C. for 1 h and at room temperature for 2 h it is added to 30 ml of ice-water. The solid is filtered off and dried in vacuo. 3.3 g (8.2 mmol, 82%) of 2-hexadecyloxy-6-methyl-4H-3,1-benzoxazin-4-one are obtained in the form of a pale yellow coloured solid with a melting point of 67° C. (literature: 72-73° C., WO 00/40569).

$^1$H-NMR (CDCl$_3$, 400 MHz): δ=0.86 ppm (t, J=6.6 Hz, 3H), 1.24-1.42 (m, 26 H), 1.75-1.82 (m, 2H), 2.40 (s, 3H), 4.41 (t, J=6.8 Hz, 2H), 7.30 (d, J=8.3 Hz, 1H), 7.51 (dd, J=8.2, 1.9 Hz, 1H), 7.90 (d, J=0.9 Hz, 1H).

The $^1$H-NMR data agree with the literature data from WO-A 00/40569.

What is claimed is:

1. The Compound of the formula (2″)

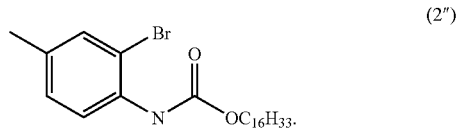

(2″)

* * * * *